United States Patent [19]

Gale et al.

[11] Patent Number: 4,505,703
[45] Date of Patent: Mar. 19, 1985

[54] FLUID RECEIVING RECEPTACLE HOUSING BIOCIDE DISPENSING DEVICE

[75] Inventors: Robert M. Gale, Mountain View; John Urquhart, Palo Alto, both of Calif.

[73] Assignee: ALZA Corporation, Palo Alto, Calif.

[21] Appl. No.: 428,342

[22] Filed: Sep. 29, 1982

[51] Int. Cl.³ .............................................. A61M 1/00
[52] U.S. Cl. ..................................... 604/317; 604/82; 604/92; 422/106
[58] Field of Search ................ 422/106, 264; 128/760, 128/762, 766, 767; 604/82, 92, 318, 322–326, 317; 222/190

[56] References Cited

U.S. PATENT DOCUMENTS

| | | | |
|---|---|---|---|
| 3,312,221 | 4/1967 | Overment | 604/323 |
| 3,521,306 | 7/1970 | Jacobs | 4/228 |
| 4,236,517 | 12/1980 | Langston | 604/323 |
| 4,386,930 | 6/1983 | Cianci | 128/767 |

*Primary Examiner*—C. Fred Rosenbaum
*Assistant Examiner*—J. L. Kruter
*Attorney, Agent, or Firm*—Paul L. Sabatine; Edward L. Mandell; Steven F. Stone

[57] ABSTRACT

A patient-care apparatus is disclosed for providing a biocide for controlling the presence of unwanted pathogens in a liquid. The patient-care apparatus comprises a container having means for maintaining a biocide dispensing device in a position in the container such that it dispenses an amount of biocide relative to the amount of liquid present in the container.

2 Claims, 7 Drawing Figures

FLUID RECEIVING RECEPTACLE HOUSING BIOCIDE DISPENSING DEVICE

FIELD OF THE INVENTION

This invention pertains to a fluid receiving receptacle housing a biocide dispensing device. The device dispenses the biocide into a fluid that contacts its surface, with the device releasing the biocide in an increasing amount as the volume of fluid increases in the receptacle and contacts a larger surface area of the device.

BACKGROUND OF THE INVENTION

It is now generally acknowledged that, if urine drains through an indwelling catheter into a receptacle that does not contain a biocide, then contaminating, unwanted pathogens will multiply rapidly in the receptacle. The presence of the pathogens can lead to serious infections of the urogenital tract in catheterized medical, surgical, gynecological, and urological patients. Since the indwelling catheter and the fluid receptacle are an important component of patient care, patentees Langston, Leeper and Wong in U.S. Pat. No. 4,241,733 provided a patient-care apparatus comprising a container with a device in the container that dispenses formaldehyde for eliminating pathogens, thereby significantly enhancing the practical value and the usefulness of the patient-care apparatus. The device dispensed the biocide formaldehyde at a constant rate that is essentially independent of the volume of fluid present in the container.

It will be appreciated by those versed in the present art that an improvement can be provided in the patient-care apparatus by making available a patient-care apparatus wherein the device dispenses a biocide in an amount corresponding to the volume of fluid in the container. That is, the device dispenses a small amount of biocide when the volume of fluid in the container is small, thereby avoiding an unnecessary high concentration of biocide in the container; and, the device dispenses a correspondingly larger amount of biocide when the volume is larger, thereby providing an amount of biocide needed for substantially eliminating unwanted pathogens.

OBJECTS OF THE INVENTION

Accordingly, it is an immediate object of the present invention to provide an improvement in patient-care apparatus, which improvement increases the usefulness of the apparatus in the management of patients in traurethral catheter drainage system.

Another object of the present invention is to provide a patient-care apparatus comprising in combination a receptacle for receiving a fluid and a device in the receptacle which device dispenses a biocide in an increasing amount as the volume of fluid increases in the receptacle.

It is a further object of this invention to provide a patient-care apparatus comprising in combination a fluid receiving receptacle housing a biocide dispensing device, which device is positioned and adapted for releasing increasing amounts of biocides as an increasing volume of fluid drains into the receptacle thereby substantially preventing the multiplication of, and controlling the migration of pathogens from the receptacle into a catheterized patient.

Yet still a further object of the invention is to make available to the medico-surgical arts a patient-care urinary drainage collection system housing a dispensing device having a shape exposing a constantly increasing area for releasing a constantly increasing amount of an antipathogenic agent, and which device embraces inventive simplicity, is inexpensive to make and is disposable.

Still yet a further object of the invention is to provide a dispensing device consisting essentially of a polymer containing a biocide, which biocide is released in the presence of moisture that enters a receptacle in an amount needed for discouraging the growth of pathogenic organisms in the moisture in the receptacle as its volume increases in the presence of the biocide dispensing device.

These and other objects of the present invention will become more apparent upon a consideration of the drawings, the specification, and the accompanying claims.

SUMMARY OF THE INVENTION

This invention concerns a patient-care apparatus, comprising in combination a receptacle for receiving and storing a biological fluid; an inlet port in the receptacle for establishing fluid passage between the interior and the exterior of the receptacle; an exit port for letting fluid leave the receptacle; and, a device in the receptacle for substantially controlling the presence of pathogens in the receptacle. The device consists of a body formed of a polymeric material that is a reservoir for containing a biocide and it has an exposed surface for releasing the biocide. The surface is contacted by the internal, fluid environment of the receptacle, and it is increasingly contacted by fluid as fluid fills the receptacle, whereby the surface releases larger amounts of biocide for controlling the presence of pathogens.

BRIEF DESCRIPTION OF THE DRAWINGS

In the drawings, which are not drawn to scale, but are set forth to illustrate various embodiments of the invention, the figures are as follows.

In the specification and the drawings, like parts in related figures are identified by like numbers. The terms appearing earlier in the specification and in the description of the drawings, as well as embodiments thereof are further described elsewhere in the disclosure.

DETAILED DESCRIPTION OF THE DRAWINGS

Figure 1:
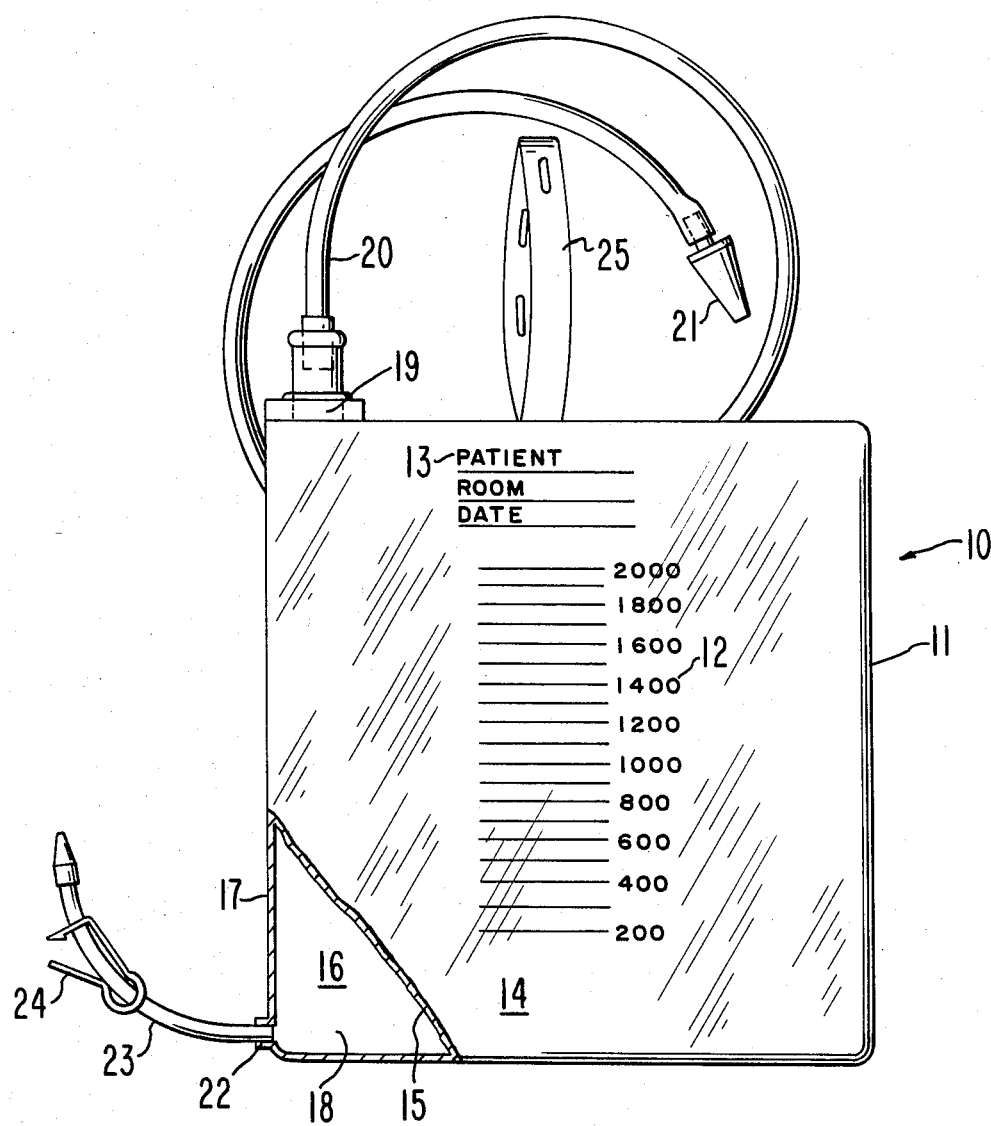
FIG. 1 is a frontal view of a patient-care apparatus showing a receptacle in opened section for illustrating the structure of the receptacle.

Turning now to the drawings in detail, which are examples of various embodiments of the invention, and which examples are not to be construed as limiting the invention, one embodiment of a novel patient-care apparatus is indicated in FIG. 1 by the numeral 10. In FIG. 1, apparatus 10 comprises a receptacle 11 that is a container for receiving and storing a biological fluid, not shown. Receptacle 11 has both a volumetric scale 12 thereon for indicating the volume of fluid in receptacle 11, and a patient identification 13 area for indicating the origin of the biological fluid. Receptacle 11 of FIG. 1 is made with a front wall 14 with a section removed 15 for illustrating its back wall 16. Front wall 14 and back wall 16 are joined around their periphery 17 to form and define an internal space 18, which is a chamber for receiving a fluid. Front wall 14 and back wall 16 are made from a pair of thin, flat, flexible plastic sheets such as polyethylene, polypropylene, and the like. Preferably, front wall 14 is made from a transparent plastic such as plasticized polyvinyl chloride and rear wall 16 is made of an opaque plastic such as polyvinyl chloride containing titanium dioxide. In this embodiment, the internal contents are visible as wall 14 and wall 16 arranged back-to-back against each other highlight the internal contents of receptacle 11.

Receptacle 11 has an inlet port 19 for receiving incoming catheter 20 that establishes fluid communication between the interior and the exterior of receptacle 11. Drainage catheter 20 has an adapter 21 attached to one end thereof for receiving an incoming catheter, not shown, from a catheterized patient. An outlet port 22 is positioned at the bottom of receptacle 11 distant from inlet 19. A receptacle drainage tube 23 is connected to outlet port 22, and it is equipped with a pinch clamp 24 for controlling the volume of fluid drained from receptacle 11. A hanging strap 25 is suitably attached to receptacle 11 for suspending receptacle 11 in a fluid receiving position at the bedside of a catheterized patient. Receptacle 11 houses in its internal space 18 a dispensing device, not shown in FIG. 1, that releases a biocide for controlling the presence of pathogens in receptacle 11.

Figure 2:
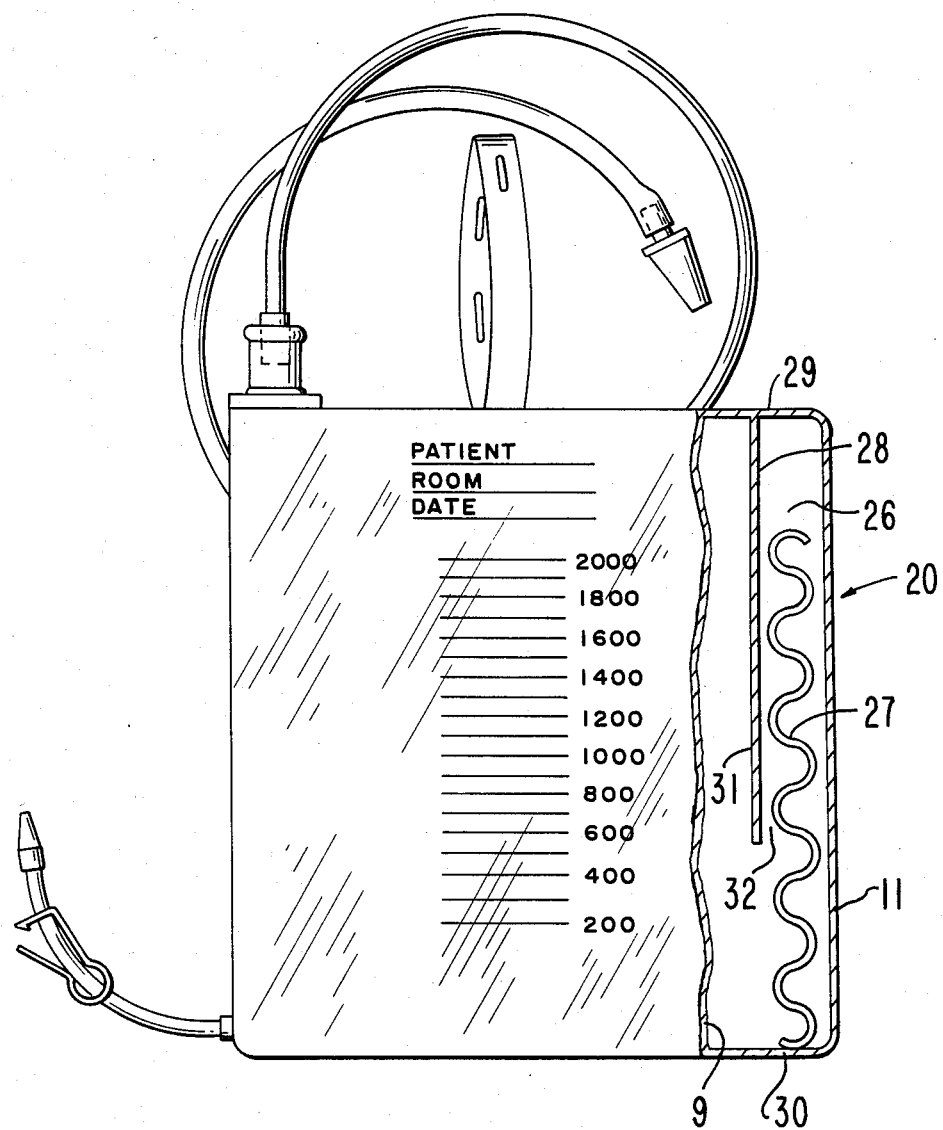
FIG. 2 is a frontal view of the patient-care apparatus illustrating in opened-section a receptacle housing a dispensing device in releasing position.

FIG. 2 illustrates a patient-care apparatus 20 that embraces many of the features of apparatus 10 of FIG. 1. In FIG. 2, the illustrated apparatus is made from transparent plastic and with a section 9 of its front panel cut away for depicting its internal structure. Apparatus 20 of FIG. 2 is structurally distinct from apparatus 10 of FIG. 1 by an internal pocket 26 for housing a device 27 for dispensing a biocide. Pocket 26 is opened at its entrance 32, and pocket 26 is formed separately in receptacle 11 by an internal wall 31 that extends about ¾ of the distance from top 29 towards bottom 30 of receptacle 11. The opened space from entrance 32 to the bottom 30 of receptacle 11 freely lets fluid in receptacle 11 contact device 27. Device 27 is a continuous S-shaped solid filament, and it is sized and adapted for easy placement and retention in pocket 26. Device 27 is formed of a polymer containing a biocide. In operation, as fluid enters receptacle 11 and touches device 27, thereby causing it to dispense biocide in an amount needed for controlling the pathogens in the fluid. Then, as more fluid enters receptacle 11 and rises in the receptacle, it contacts a larger proportion of the releasing surface of device 27 causing it to correspondingly release the needed amount of biocide. Eventually, as fluid enters and rises in pocket 26, it continuously contacts more of device 27, and correspondingly urges device 27 to meter more biocide into the fluid for controlling the presence of pathogens in the fluid.

Figure 3:
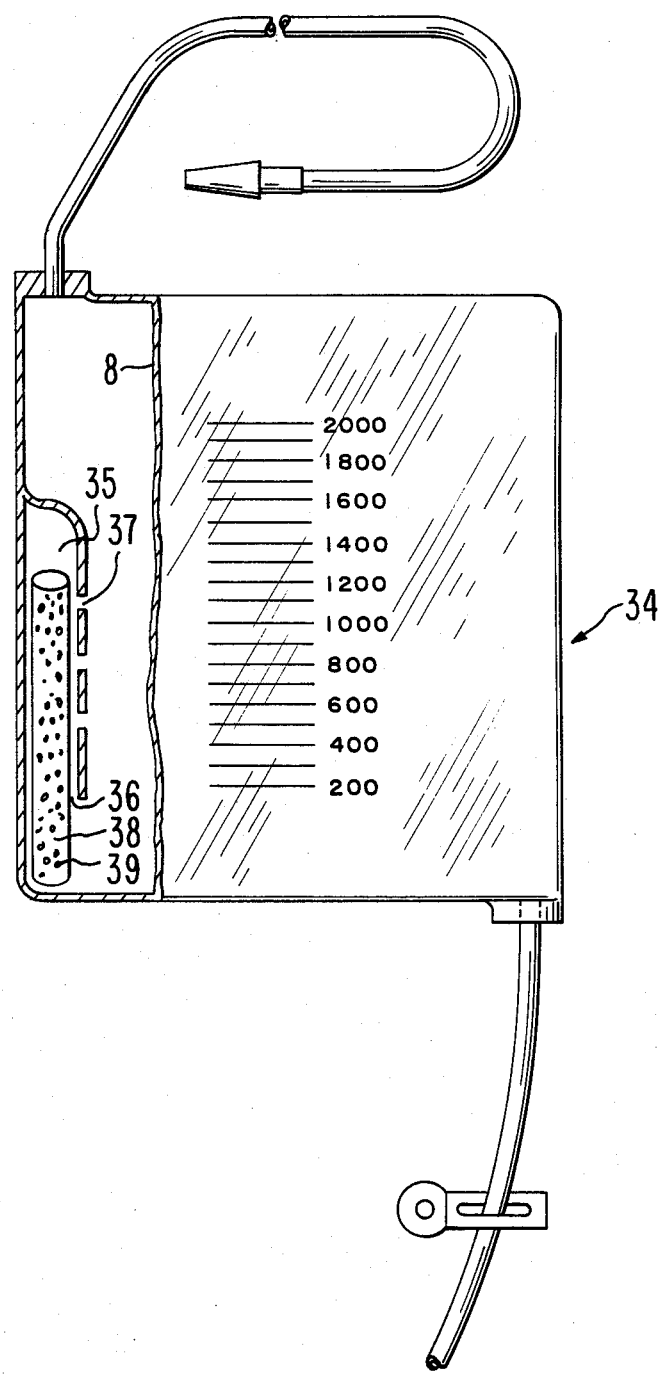
FIG. 3 is a view of the patient-care apparatus in opened section illustrating a receptacle housing another embodiment of a dispensing device.

FIG. 3 illustrates another embodiment of the invention. FIG. 3 illustrates a patient-care apparatus 34 manufactured with the features described above, and it is made of fluid impermeable material with a section 8 removed for viewing the structure thereof. In the present embodiment, apparatus 34 consists additionally of an internal side pocket 35 formed integral within the fluid receiving receptacle. The side pocket is similar to pocket 26 described in FIG. 2, having an opening 36 and additional holes 37 for letting greater volume of fluid enter the pocket. Side pocket 35 houses a dispensing device 38 having a rod-like shape and formed of a polymeric material containing a biocide 39. In operation, device 38 meters biocide 39 into a changing volume of fluid in a manner as described in FIG. 2.

Figure 4:
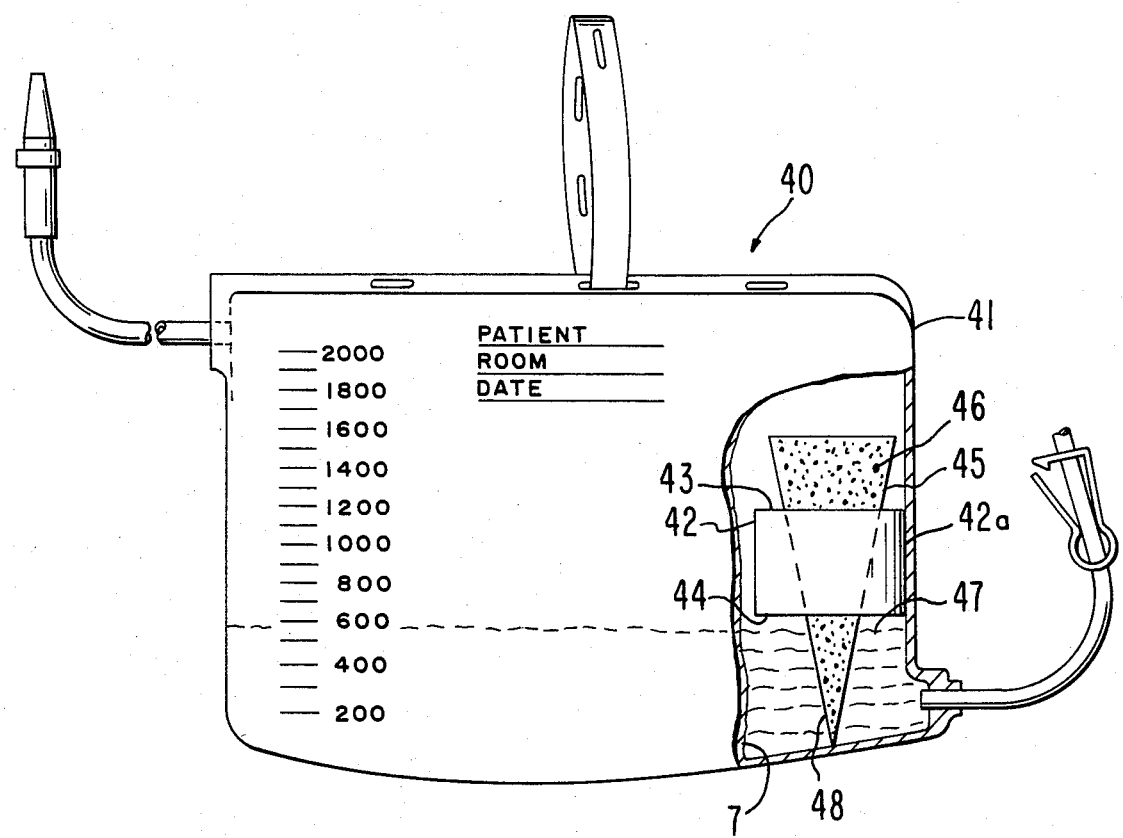
FIG. 4 is a view of another embodiment of the invention illustrating a receptacle in opened section housing a dispensing device having a surface of increasing area and supported by the receptacle.

FIG. 4 illustrates another embodiment of the invention. FIG. 4 shows a patient-care apparatus 40 comprising a receptacle 41 made of a fluid impermeable material in opened section 7 for seeing its internal content. Receptacle 41 has an internal sleeve 42 fixed 42a to the inside boundary of receptacle 41. Sleeve 42 has openings at its top 43 and at its bottom 44 for receiving a dispensing device 45. Device 45 is generally of triangular shape and it is positioned in sleeve 42 such that its exposed surface increases ascending from the bottom to the top of receptacle 41. Device 45 is made of a sheet of polymeric material containing a biocide, represented by dots 46. In operation, device 45 releases biocide 46 into a fluid 47 in receptacle 41, and as the level of fluid 47 rises, device 45 releases (a) biocide 46 at the device-fluid interface 48, and (b) in an increasing amount corresponding to the increased surface-fluid interface arising by device 45 being contacted by more fluid. In this manner, the device provides an amount of biocide needed for controlling the pathogens in the volume of fluid in the receptacle at any given time.

Figure 5:
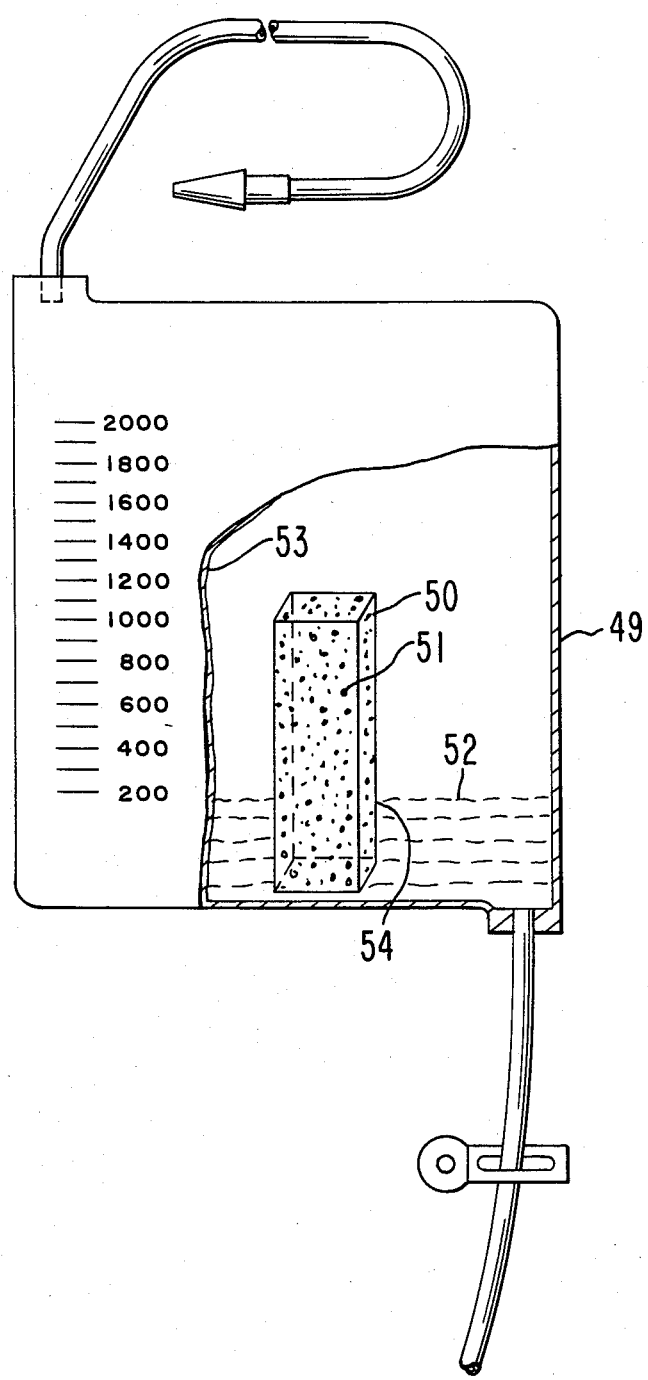
FIG. 5 is a view of another embodiment of the invention illustrating a receptacle in opened section housing a dispensing device positioned in the receptacle such that a large area of its surface is contacted as the amount of fluid increases in the receptacle.
Figure 6:
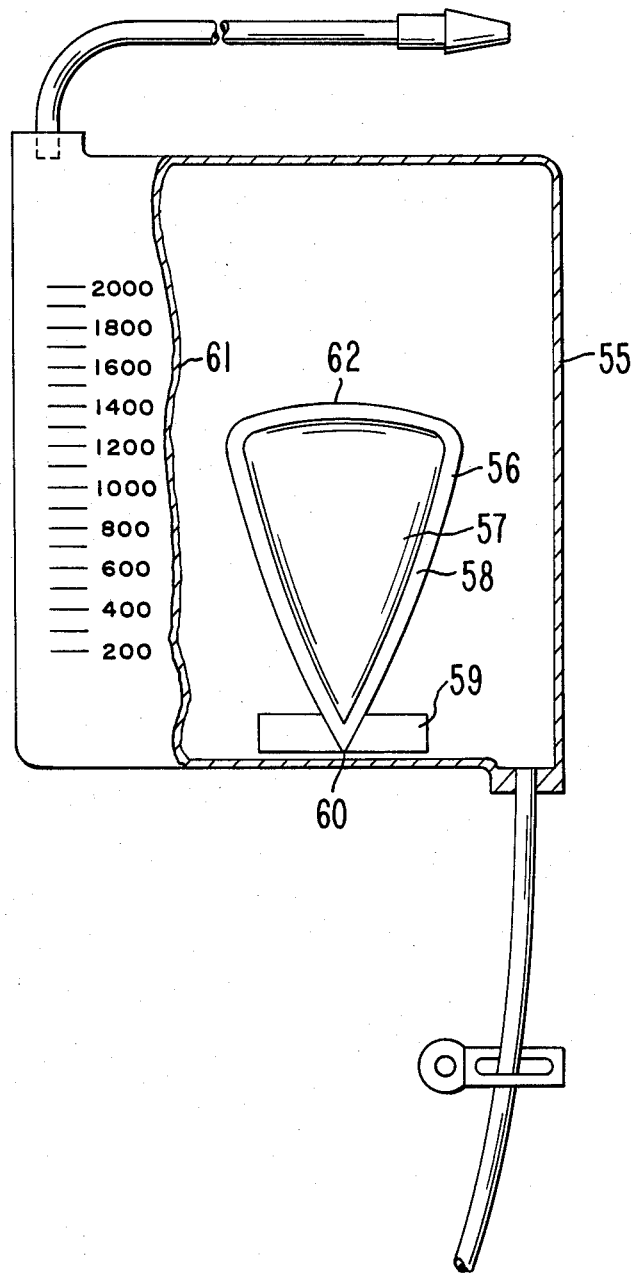
FIG. 6 is a view of an embodiment of the invention that illustrates a fluid receiving receptacle in opened section containing a dispensing device having an exposed, increasing surface from its bottom to its top, for releasing more biocide as fluid contacts the device from its bottom to its top.
Figure 7:
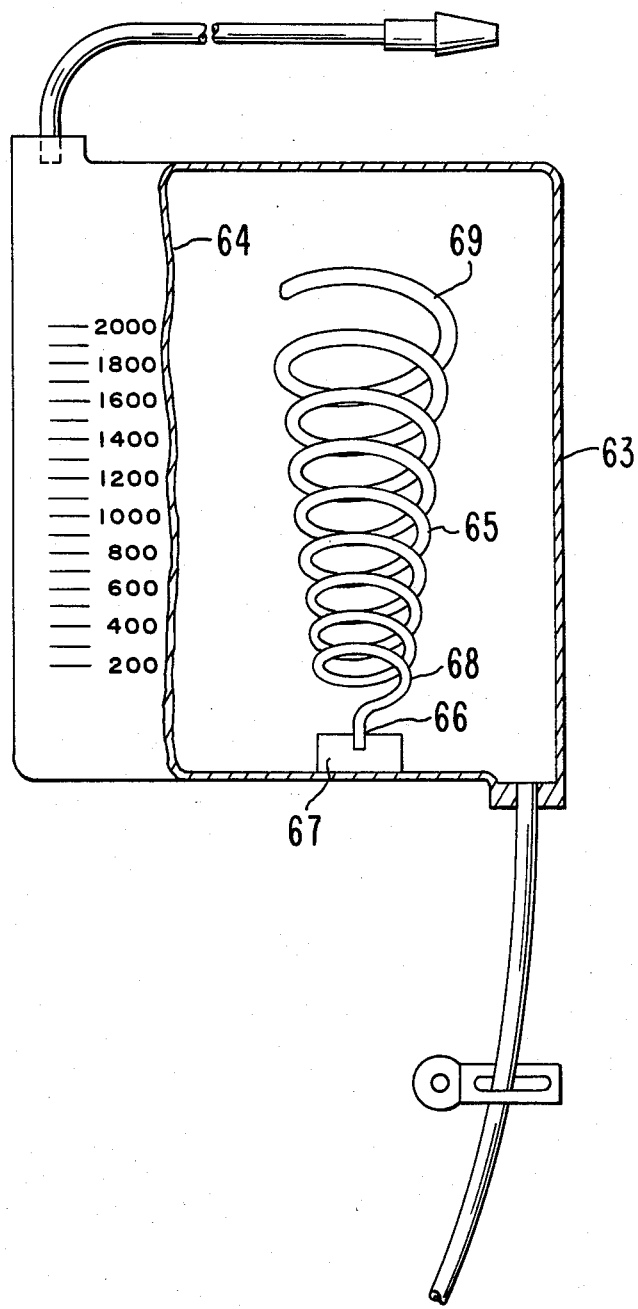
FIG. 7 is a view of another embodiment of the invention that depicts in opened section a receptacle containing a dispensing device adapted, shaped and sized for dispensing larger amounts of biocide as the level of fluid rises in the receptacle.

FIGS. 5, 6, and 7 illustrate further embodiments of the invention, with a section of their wall removed for depicting the internal structure of the receptacle, wherein a dispensing device having an internal reservoir for containing a biocide is placed in a receptacle in a self-supporting biocide dispensing position, that is essentially independent of support imparted by the receptacle. In FIG. 5, illustrated by an opened section 53, receptacle 49 houses a dispensing device 50 containing biocide 51 that is released into fluid 52. Device 50 is of rectangular shape, it has a length greater than its width, and it is placed in the receptacle such that its length parallels an imaginary axis that extends from the top to the bottom of receptacle 49. In this manner, device 50 dispenses biocide 51 only at the device-fluid interface 54, and as the interface increases the device dispenses more biocide.

FIG. 6 illustrates a receptacle 55 in opened view at 61 housing a biocide dispensing device 56, which device 56 comprises a sheet of polymer 57 supported by a rim 58.

Device 56 is shaped like a flat triangle and it is held in an upright position by a base member 59 that receives and holds the apex 60 of device 55. Device 55 contains a biocidally effective amount of biocide, its surface increases ascending from apex 60 to its top 62, and it operates in the manner described heretobefore.

FIG. 7 illustrates a receptacle 63, in opened view 64, containing a device 65 manufactured as a resilient spiral. The device 65 is made of a polymer containing a biocide. Device 65 is supported at its smallest terminal 66 by a support member 67. The successive turns of the device increase in size ascending from its first curved surface 68 to its top curved surface 69 for dispensing increasing amounts of biocide in the manner described above.

ADDITIONAL DESCRIPTION OF THE INVENTION

The device used for containing and delivering a biocide for the purpose of the invention consists of a body formed of a polymeric material that releases a biocide in the presence of a fluid, mainly urine. Representative polymers suitable for forming the body of the device include acrylic polymers and copolymers of methacrylate, ethylacrylate, ethylmethacrylate, and methacrylate; homopolymers and copolymers of vinyl chloride including vinyl chloride-vinyl acetate copolymer; chlorinated vinyl chloride; polyethylene; polypropylene; ethylene-propylene copolymer; chlorinated polyethylene; ethylene-vinyl acetate copolymer; styrene-butadiene copolymer; acrylonitrite-styrene-butadiene terpolymer; polyvinylidene chloride; vinyl chloride-vinylidene chloride copolymer; vinylidene chloride-acrylonitrite copolymer; vinylidene chloride-acrylate ester copolymer; polybutylene terephthalate; vinyl chloride-acrylate ester copolymer; polyamides; polyvinyl acetals; polyvinyl formal; polyvinyl butyral; polyethers; polyesters; polyurethanes; chlorosulfonated polyolefins; polyisoprene; polybutadiene; silicone; and the like.

The biocide that can be housed in the dispensing device that comprises a polymeric body as a means for housing biocides in various physical-chemical forms such as solid, semi-solid, liquid and the like, and the biocides broadly include bis-biguanido-hexane; chlorhexidine; alexidine; hexachlorophene; benzalkanium chloride; sulfonamides; phenol; and, paraformaldehyde. The amount of biocide housed in a device can vary depending on the need, and it will usually be about 0.001% to 60% by weight based on the weight of the dispensing device. Generally, the device will meter a biocidally effective amount for controlling the presence of pathogens in the receptacle containing a fluid, such as urine.

The expression "controlling the presence of pathogens" as used herein means in the general context of this invention, killing, preventing and/or retarding the presence, or propagation of micro-organisms in the fluid receiving receptacle. The phrase "unwanted, micro-organisms" include the fungi *Aspergillus niger, Aspergillus flavus, Rhizopus nigruians, Cladosporium herbarium; Epidermaphyton floccosum, Trichophyton mentagrophetes, Histoplasma capsulatum,* and the like. The terms pathogens and micro-organisms include also bacteria such as *Pseudomonas aerugenosa, Escherichia coli, Proteus vulgaris, Staphyloccus aureus, Streptococcus faecalis, Klebsiella, Enterobacta aerogenes, Proteus mirabilis,* and other gram-negative staining bacteria, and gram-positive staining bacteria. The terms also embrace yeast such as *Saccharomyces cerevisiae, Candida Albicans,* and the like. Additionally, spores of micro-organisms, viruses, and the like are within the intent of the invention.

The following example will serve to further illustrate the present invention, but the invention is not intended to be limited thereto.

A dispensing device is made as follows: first, 45 grams of powdered, white solid polymeric paraformaldehyde is blended for 10 to 15 minutes at 35° to 45° C. on a two-roller mill with 55 grams of powdered, transparent ethylenevinyl acetate copolymer, having a vinyl acetate content of 28% by weight, to produce a film consisting essentially of a homogenous dispersion of paraformaldehyde in the copolymer. Next, the film is ground in a rotary-knife grinder to produce particles sized 1/16 to ⅛ inches, average size, and the particles then transferred to the hopper of an extruder. Finally, the particles are extruded through a rod forming dye at 60° to 70° C. to yield the dispensing device. The device had a diameter of 6 mm and a length of 5 cm. The dispensing device, when housed in a pocket of a receptacle, and on contact with fluid, exhibited a steady-state delivery of a biocidally effective amount of free formaldehyde, at the rate of 220 $\mu$g/hr-cm of device. This level is sufficiently low to prevent micro-organism growth, and the amount released is increased as more of the device is moistened by fluid. The devices are stored in dry packages to prevent premature contact with moisture before they are used for their intended effect.

It will be understood by those versed in the biocide art that in the light of the present specification, drawings, and the claims, many embodiments of this invention can be made without departing from the scope of the invention. Accordingly, it is to be understood the invention is not to be construed as limited, but it embraces all equivalents inherent herein.

We claim:

1. An improvement in a patient-care apparatus comprising in combination: (a) a receptacle for receiving and storing a biological fluid; an inlet port in the receptacle for establishing fluid passage between the interior and the exterior of the receptacle; and (b) a device in the receptacle for substantially controlling the presence of pathogens in the receptacle, said device consisting essentially of a body sized and adapted for prolonged placement in the receptacle and having an exposed surface that is contacted by fluid that enters the receptacle, the body being formed of a polymeric material containing a biocide, which biocide is released at the surface into the fluid for controlling the presence of pathogens; and wherein the improvement comprises the device being shaped such that a larger cross-sectional surface area is contacted by the fluid as the volume of fluid that enters the receptacle increases over the entire surface of the device and throughout a substantial portion of the height of the receptacle for releasing an increasing amount of biocide into the fluid that enters the receptacle and wherein the device is constrained in the receptacle such that a minimum of its exposed surface is at substantially the lower wall of the receptacle and is contacted by fluid that initially enters the receptacle for releasing biocide thereto.

2. A patient-care apparatus comprising in combination:

(a) a container for receiving and storing a biological fluid;

(b) an inlet in the container for establishing fluid passage between the interior and the exterior of the container;

(c) pocket constraining means secured along a wall of the container having an opening for establishing communication between the inside of the pocket constraining means and the container;

(d) a device in the container that is out of the direct flow path of the fluid, extending from substantially the lower wall of the container to a substantial portion of the height thereof and is constrained in the pocket constraining means for substantially controlling the presence of pathogens in the container; the device consisting essentially of:

(1) a body sized and adapted for placement in the container and into the pocket, the body having an exposed surface that is contacted by fluid that enters the container and the pocket constraining means, and which body is formed of a polymeric material;

(2) a biocide in the body which is released at the surface into fluid for controlling the presence of pathogens; and, (3) wherein, the device is positioned in the container and in the pocket constraining means with at least some of its surface available for contacting by fluid that initially enters the container for releasing biocide thereto, and as fluid volume increases in the container and enters the pocket more surface of the device is contacted by the fluid.

* * * * *